United States Patent
Koftis et al.

(10) Patent No.: US 8,754,261 B2
(45) Date of Patent: Jun. 17, 2014

(54) PROCESS FOR THE PREPARATION OF O-DESMETHYL-VENLAFAXINE AND SALTS THEREOF

(75) Inventors: Theoharis V. Koftis, Salonika (GR); Ioanna Georgopoulou, Salonika (GR); Alexandros Strongilos, Koropi Attikis (GR); Fotini Liepouri, Koropi Attikis (GR); Theodoros Panagiotidis, Salonika (GR); Alexandra Lithadioti, Salonika (GR)

(73) Assignee: Pharmathen S.A., Pallini Atikis (GR)

( * ) Notice: Subject to any disclaimer, the term of this patent is extended or adjusted under 35 U.S.C. 154(b) by 0 days.

(21) Appl. No.: 13/515,871

(22) PCT Filed: Dec. 16, 2009

(86) PCT No.: PCT/EP2009/009022
§ 371 (c)(1),
(2), (4) Date: Jun. 14, 2012

(87) PCT Pub. No.: WO2011/072703
PCT Pub. Date: Jun. 23, 2011

(65) Prior Publication Data
US 2012/0253074 A1    Oct. 4, 2012

(51) Int. Cl.
C07C 211/00    (2006.01)

(52) U.S. Cl.
USPC .................................................. 564/336

(58) Field of Classification Search
None
See application file for complete search history.

(56) References Cited

FOREIGN PATENT DOCUMENTS

| EP | 0112669 A2 | 7/1984 |
|----|------------|--------|
| IL | WO2010008735 A2 | 1/2010 |
| SI | WO2005058796 A2 | 6/2005 |
| SI | WO2009138234 A1 | 11/2009 |
| WO | WO02064543 A2 | 8/2002 |

*Primary Examiner* — Clinton Brooks
(74) *Attorney, Agent, or Firm* — AKC Patents; Aliki K. Collins

(57) ABSTRACT

The present invention relates to a novel process for the preparation of O-desmethyl venlafaxine (ODV) and the pharmaceutically acceptable salts thereof, wherein it comprises (i) provision of spiro-venlafaxine compound as intermediate; (ii) conversion of spiro-venlafaxine intermediate into ODV free base in a one-pot process; and (iii) optionally conversion ODV free base into pharmaceutically acceptable salts. The present invention further relates to novel processes for the preparation of crystalline salts of ODV-succinate and ODV-oxalate.

7 Claims, 1 Drawing Sheet

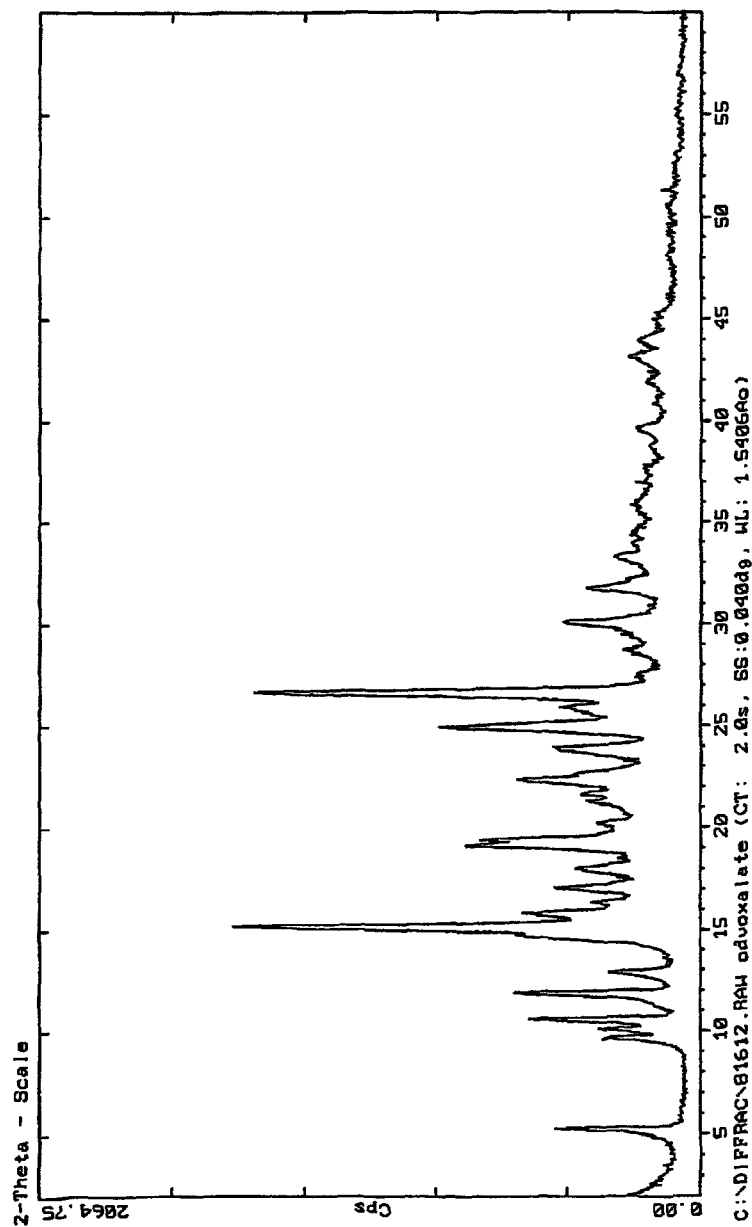

PROCESS FOR THE PREPARATION OF O-DESMETHYL-VENLAFAXINE AND SALTS THEREOF

TECHNICAL FIELD OF THE INVENTION

The present invention relates to an improved process for the preparation of O-desmethyl venlafaxine (ODV) and pharmaceutical acceptable salts or derivatives thereof and in particular to a cost-effective process for the preparation of essentially pure ODV and pharmaceutically acceptable salts or derivatives thereof suitable for large scale production.

BACKGROUND OF THE INVENTION

O-desmethyl venlafaxine (ODV), also commonly referred to as Desvenlafaxine, is chemically designated as 4-[2-dimethylamino-1-(1-hydroxycyclohexyl) ethyl]phenol. ODV is the major active metabolite of Venlafaxine and has a similar therapeutic profile to the profile of Venlafaxine, which is an active pharmaceutical ingredient indicated for the treatment of depression, anxiety and panic disorder.

ODV is presented by the structure of Formula I:

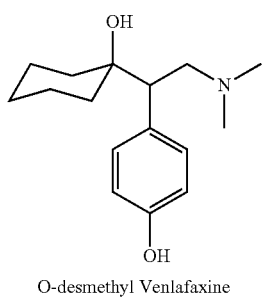

(Formula I)

O-desmethyl Venlafaxine

The molecule of ODV has one optically active center. As used herein, the term "ODV" refers to racemic ODV, unless stated otherwise.

Various methods are already known for the preparation of ODV or salt thereof due to its useful properties. Prior art processes for the preparation of Venlafaxine and ODV present the disadvantage of non-satisfactory purity and yield of the product. Moreover, many of the known processes for the preparation of Venlafaxine and ODV are not suitable to be adapted for large scale production. Furthermore, the compound obtained from these prior art processes often comprises significant amounts of unwanted by-products and the reaction may require a long period of time to be completed.

Several known prior art processes for the preparation of O-desmethyl venlafaxine involve demethylation of Venlafaxine. Such reaction requires crucial conditions because, on one hand, the methyl phenoxy group is very stable against nucleophilic substitution and on the other hand, the tertiary hydroxyl and the dimethylamine groups in the same molecule are susceptible to nucleophlilic attack. As a result, these processes often utilize conditions that are not suitable for large scale production.

EP-A-112 669 and its corresponding U.S. Pat. No. 4,535,186 discloses a process for the preparation of Venlafaxine and ODV by hydrogenating the O-benzyl protected precursor, which is prepared by coupling p-benzyloxyphenyl acetamide and cyclohexanone followed by reduction using lithium aluminum hydride.

This document discloses various reduction conditions as under i) Pd/C and hydrogen in ethanol+THF media, ii) Lithium aluminium hydride in acid media, iii) Rhodium Alumina in ammoniacal ethanol, iv) Borane tetrahydrofuran complex.

However the process of the above patent has the disadvantage that the addition of n-butyl lithium to 4-methoxyphenyl acetonitrile is hazardous, requiring high safety measures and great attention in handling butyl lithium, in order to avoid any unwanted incidents during the preparation process and thus said process is not suitable to be adapted for industrial manufacture.

WO 00/59851 discloses a method for the preparation of O-desmethyl venlafaxine Desvenlafaxine by reacting Venlafaxine with lithium diphenylphosphide, which is generated in-situ by slow addition of n-butyl lithium to diphenylphosphine in THF at a temperature below 0° C. THF solution of n-butyl lithium is extremely dangerous to be used in industrial production because it reacts actively with moisture in the air and generates hydrogen gas along with large amount of heat, which makes it highly explosive.

Further, WO 02/64543 discloses another method of demethylating Venlafaxine using an alkali metal salt of trialkyl borohydride, e.g. L-selectride, to obtain O-desmethyl venlafaxine. This process is not suitable for industrial production because hydrogen gas is formed during the process. Various boron-containing byproducts are also formed and pose harmful risk to the personnel and the environment.

Although each of the above documents represents an attempt to overcome the disadvantages in the prior art, there still exists a need for a cost-effective and safer process for large scale production of essentially pure O-desmethyl venlafaxine and the pharmaceutically acceptable salts thereof, which employs low toxic materials, moderate reaction conditions and capable of providing stable crystalline O-desmethyl venlafaxine and salts thereof in higher yield with higher purity.

SUMMARY OF THE INVENTION

It is, therefore, an object of the present invention to provide an improved process for the preparation of essentially pure O-desmethyl venlafaxine and pharmaceutically acceptable salts or derivatives thereof, which overcomes the deficiencies of the prior art and provide a cost effective large scale manufacture process without scarifying the quality of the product.

Another object of the present invention is to provide an improved method for the preparation of O-desmethyl venlafaxine and pharmaceutically acceptable salts or derivatives thereof by using milder and safer reaction conditions that helps protecting the environment and the personnel.

Further object of the present invention is to provide a method of producing O-desmethyl venlafaxine and pharmaceutically acceptable salts or derivatives thereof, in which the impurities and contaminants are minimized, by selecting the appropriate reactants, solvents, catalysts, intermediates as well as optimized reaction conditions.

In accordance with the above objects of the present invention, a process for the preparation of O-desmethyl venlafaxine and slats or derivatives thereof is provided comprising the following steps:

(a) Provision of compound of (5RS)-5-(4-methoxyphenyl)-3-methyl-1-oxa-3-azaspiro[5,5]undecane, namely the spiro-venlafaxine;

(b) conversion of spiro-venlafaxine into spiro-venlafaxine hydrochloride salt and isolation of said salt in pure form;

(c) obtaining O-desmethyl Venlafaxine free base in a one-pot process using spiro-venlafaxine hydrochloride salt as starting material, wherein said one-pot process of step is performed by first O-demethylating of the spiro-venlafaxne hydrochloride obtained from step (b) and subsequently treating the reaction mass with paraformaldehyde, formic acid and water at elevated temperature, preferably from about 105 to about 110° C., to obtain O-desmethyl Venlafaxine free base.

In another embodiment, the present invention provides a process for the preparation O-desmethyl Venlafaxine oxalate and a compound obtained according to said process.

Preferred embodiments of the present invention are set out in dependent claims 2 to 7.

Other objects and advantages of the present invention will become apparent to those skilled in the art in view of the following detailed description.

BRIEF DESCRIPTION OF THE FIGURES

FIG. 1 shows a powder XRD pattern of crystalline O-desmethyl-Venlafaxine oxalate (ODV-oxalate) prepared according to the present invention and in particular according to Example 4.

DETAILED DESCRIPTION OF THE INVENTION

The present invention relates to an improved process for the preparation of O-desmethyl-Venlafaxine and pharmaceutically acceptable salts or derivatives thereof, which is characterized in substantially milder and safer reaction conditions, without scarifying the yield and quality of the product.

In the present invention, it has been surprisingly found that performing demethylation on spiro-venlafaxine of the chemical structure Formula II, we can circumvent the disadvantages of demethylating Venlafaxine, since the sensitive tertiary hydroxyl and the dimethylamine groups are incorporated in a stable six-member ring and thus, the side reactions can be eliminated.

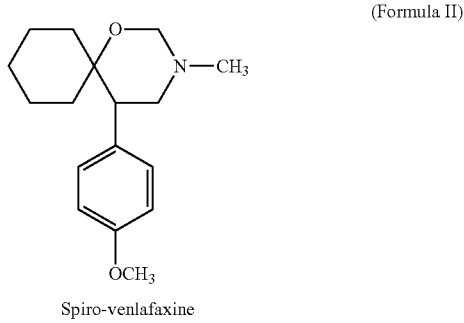 [SMILES: COc1ccc(C2CN(C)COC23CCCCC3)cc1]

(Formula II)

Spiro-venlafaxine

Spiro-venlafaxine is an intermediate formed during the synthesis of Venlafaxine and can be obtained in pure form by early termination of the reaction. Thus, the use of spiro-venlafaxine instead of Venlafaxine as an intermediate for the preparation of O-desmethyl-Venlafaxine results in substantially reduction of the reaction time, and hence the production cost.

According to the present invention, O-desmethyl-Venlafaxine and pharmaceutically acceptable salts thereof are prepared from 1-[cyano-1-(4-methoxyphenyl) methyl]cyclohexanol, which is used as the key starting material.

The preparation of 1-[cyano-1-(4-methoxyphenyl) methyl]cyclohexanol involves the reaction of 4-methoxyphenylacetonitrile with cyclohexanone in the presence of a solvent mixture comprising a solution of basic material, such as alkali metal alkoxide, alkali amide or alkali hydride and alcohol. The solid mass obtained by the reaction is then filtered and recrystallized to provide 1-[cyano-1-(4-methoxyphenyl) methyl]cyclohexanol, which constitutes the starting material for the preparation of O-desmethyl-Venlafaxine.

The key starting material 1-[cyano-1-(4-methoxyphenyl) methyl]cyclohexanol is hydrogenated in a high pressure reactor using Pd/C as catalyst and glacial acetic acid as solvent.

The obtained hydrogenation product is subjected to methylation condition to provide compound of (5RS)-5-(4-methoxyphenyl)-3-methyl-1-oxa-3-azaspiro[5,5]undecane, namely spiro-venlafaxine. The progress of said methylation is monitored so that spiro-venlafaxine is obtained before any Venlafaxine is formed.

Spiro-venlafaxine is then treated with an iso-propanol solution of hydrochloride (IFA·HCl) to give the corresponding salt (Scheme 2). Recrystallization of crude spiro-venlafaxine hydrochloride salt in isopropanol provides spiro-venlafaxine hydrochloride in pure form.

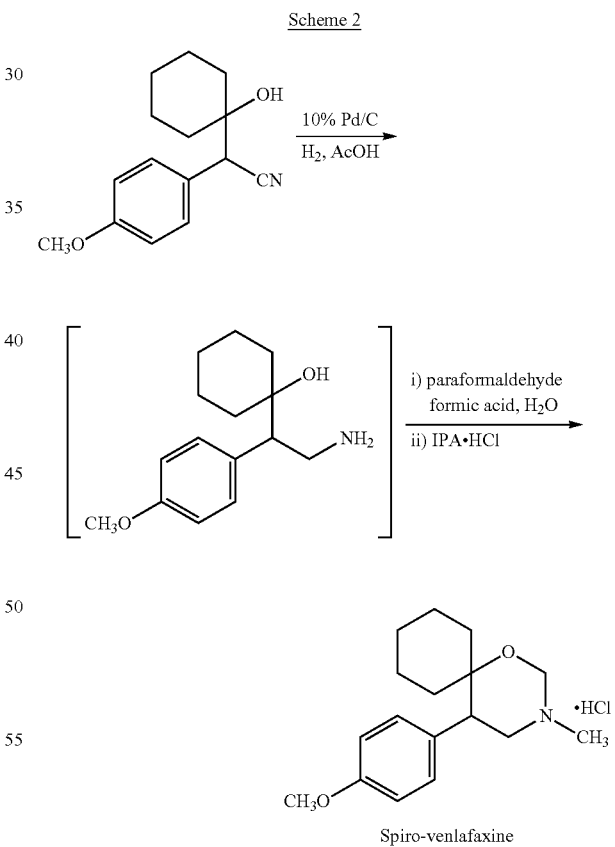

Scheme 2

Spiro-venlafaxine

Spiro-venlafaxine hydrochloride is subjected to demethylation condition to remove the O-protecting methyl group. Then the reaction mass is converted into O-desmethyl-Venlafaxine free base (Scheme 3).

Further, the O-desmethyl-Venlafaxine free base can be converted into the acid addition salt forms.

Scheme 3

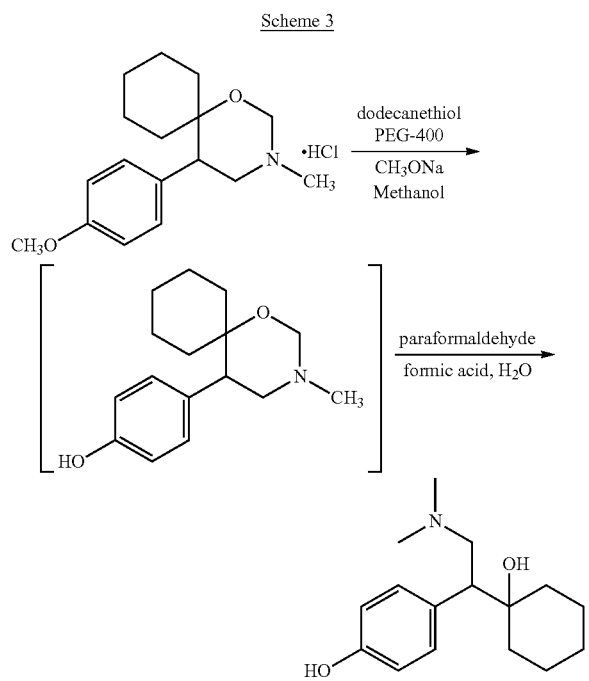

The conversion of spiro-venlafaxine hydrochloride into O-desmethyl-Venlafaxine free base is carried out in a one-pot process, which comprises O-demethylation of spiro-venlafaxine hydrochloride and in-situ ring-opening of the spiro-desvenlafaxine intermediate to provide O-desmethyl-Venlafaxine free base.

O-desmethylating spiro-venlafaxine hydrochloride is performed using alkane thiolate anion in the presence of high molecular weight polyol and alcoholic solvent at elevated temperature. The alkane thiolate anion can be generated in-situ by mixing an aliphatic thiol having 8 to 20 carbons with a base such as alkoxide.

The high molecular weight polyol can be polyethyleneglycol (PEG). Reaction solvents can be selected from aprotic or protic solvents, preferably alcoholic solvents. Reaction temperature is above 120° C., preferably 145° C. to 150° C.

The O-desmethylated spiro-desvenlafaxine intermediate is converted into O-desmethyl-Venlafaxine free base by heating the intermediate with a mixture of paraformaldehyde, formic acid and water at elevated temperature.

The thus obtained O-desmethyl-Venlafaxine free base can used to obtain O-desmethyl-Venlafaxine succinate or O-desmethyl-Venlafaxine oxalate in stable crystalline form.

O-desmethyl-Venlafaxine succinate of the present invention can be prepared by adding succinic acid to a refluxing suspension of O-desmethyl-Venlafaxine in a mixed solvent of acetone and water. The reaction mixture is cooled gradually to temperature of about 25-30° C. and stirred at this temperature for a period of time sufficient for crystallization. Further cooling the reaction mass to about 10° C. and allow the crystallization to complete. The solid is filtered and washed with acetone to obtain crystalline O-desmethyl-Venlafaxine succinate. A further recrystallization using acetone and water provides O-desmethyl-Venlafaxine succinate in pure stable crystalline form.

O-desmethyl-Venlafaxine oxalate of the present invention can be prepared by mixing O-desmethyl-Venlafaxine free base with oxalic acid in mixture of acetone and water. The mixture is heated to 50° C.-55° C. The hot solution is filtered and the filtrate is cooled to crystallize the target compound. The crystals are collected and washed with acetone to obtain crystalline O-desmethyl-Venlafaxine oxalate. A further recrystallization using acetone/ethanol as solvents provides O-desmethyl-Venlafaxine oxalate in pure stable crystalline form.

The process of the present invention will be demonstrated in more details with reference to the following examples, which are provided by way of illustration only and should not be construed as limit to the scope of the reaction in any manner.

EXAMPLES OF THE INVENTION

Example 1

Preparation of 1-[cyano-1-(methoxyphenyl) Methyl]Cyclohexanol

To a solution of sodium methoxide (99 g, 1.83 moles) in methanol (25% w/w, 396 ml) at a temperature of about –5° C., 66 ml methanol solution of 4-methoxyphenylacetonitrile (90 g, 0.6 moles) is added slowly over a period of 60 minutes and the mixture is stirred for an additional period of 120 minutes, while maintaining the temperature below 0° C. Further this mixture is cooled to a temperature of about –5° C. and 66 ml methanol solution of cyclohexanone (83.4 ml, 0.81 moles) is added over a period of 60 minutes, while maintaining the temperature below 0° C.

The reaction mass is stirred at a temperature of about 0° C. for about 48 hours and quenched with slow addition of 828 ml of water while keeping the temperature below 0° C. The precipitated solid is filtered off and washed with 72 ml of water. The resulted wet solid is dissolved in 825 ml of toluene and heated at temperature of about 50°-55° C. till a clear solution is obtained. The hot solution is then filtered, cooled slowly to a temperature of about 5°-10° C. and maintained for about 2 hours under stirring. The white solids are filtered and recrystallized with 351 ml toluene to obtain 114 g (78% yield) of 1-[cyano-1-(methoxyphenyl)methyl]cyclohexanol after vacuum drying.

Chemical Structure of the Obtained 1-[cyano-1-(methoxyphenyl)Methyl]Cyclohexanol has the Following Analytical Data:

$^1$H NMR (300 MHz, CDCl$_3$): δ/ppm 1.14-1.22 (m, 1H), 1.51-1.73 (m, 9H), 1.79 (s, 1H), 3.73 (s, 1H), 3.80 (s, 3H), 6.90 (d, 2H, J=8.5 Hz), 7.26 (d, 2H, J=8.5 Hz).

$^{13}$C NMR (75 MHz, CDCl$_3$): δ/ppm 21.4, 21.4, 25.1, 34.7, 34.9, 49.2, 55.2, 72.6, 113.9, 113.9, 119.8, 123.6, 130.5, 130.5, 159.6.

IR (λ/cm$^{-1}$): 1034, 1180, 1254, 1512, 1613, 2249, 2930, 3408.

wherein $^1$H NMR=proton nuclear magnetic resonance spectroscopy $^{13}$C NMR=carbon nuclear magnetic resonance spectroscopy IR=infrared spectroscopy δ=is the chemical shift referenced against tetramethylsilane (TMS), s, d, t and m are referred to singlet, doublet, triplet and multiplet peaks respectively.

J=the spin-spin coupling coefficient observed in $^1$H NMR measurement.

λ=the wave number in the infra-red measurements.

| Elemental analysis for $C_{15}H_{19}NO_2$: | | |
|---|---|---|
| Element % | Theoretical values | Observed (averaged) values |
| C % | 73.44 | 73.47 |
| H % | 7.81 | 7.56 |
| N % | 5.71 | 5.71 |

Example 2

Preparation of the (5RS)-5-(4-methoxyphenyl)-3-methyl-1-oxa-3-azaspiro[5,5]Undecane Hydrochloride (Spiro-Venlafaxine Hydrochloride)

A suspension of 100 g (0.408 mol) 1-[cyano-1-(methoxyphenyl)methyl]cyclohexanol in 700 ml glacial acetic acid is stirred in a high pressure reactor. 6 g 10% Pd/C is added carefully to the suspension under stirring. Subsequently, the reactor was flushed with nitrogen and hydrogen gas three times. The reaction mixture is subjected to hydrogenation at temperature of about 43-47° C. under hydrogen pressure of about 11.7 Kg/cm$^3$ for about 4 hours. Upon completion of the hydrogenation, hydrogen gas is carefully released and the reaction mass is cooled down to temperature of about 25° C. with purging inert gas. The catalyst is removed by filtration and washed with 50 ml glacial acetic acid. The filtrate is concentrated under reduced pressure at temperature of about 45-50° C. until solvent is completely removed to obtain a colorless viscous oil.

The obtained viscous oil is dissolved in 600 ml D.M. water. Paraformaldehyde (42.8 g, 1.43 mol) and formic acid (30.8 ml, 0.82 mol) are added and the reaction mixture is heated at temperature of about 53-57° C. for about 14-20 hours. Then, the reaction mixture is basified with 280 ml aqueous sodium hydroxide solution (50%, w/v), extracted with 600 ml toluene and the aqueous layer further is extracted twice with 300 ml toluene (600 ml), the organic layers are combined and washed with 200 ml 20% aqueous sodium chloride solution. The pH is adjusted to pH value about 5.5-6.0 using 10-20 ml 2N hydrochloric acid and 100 ml D.M. water. The separated organic layer is washed with 100 ml D.M. water and dried over 100 g anhydrous sodium sulphate. The inorganic salt is filtered out and washed with 100 ml toluene. The filtrate is quenched with 80 ml 4-5N isopropanolic hydrochloride solution.

The precipitated solids are stirred for about 120-180 minutes at temperature of about 25-30° C. Then the solids are filtered and dried in vacuum funnel for about 60 minutes. The wet cake is dissolved in 600 ml isopropanol under heating at reflux and the clear solution is gradually cooled at temperature of about 10-15° C. for 240 minutes. The precipitated solid is filtered out, washed with 100 ml isopropanol and dried in vacuum funnel for 60 minutes. The wet cake is dissolved in 500 ml isopropanol under heating at reflux and the clear solution is filtered through 10 g of celite bed, washed with 50 ml hot isopropanol and gradually cooled under stirring for about 240 minutes at temperature of about 10-15° C. The solid is filtered out, washed with 50 ml isopropanol and dried in vacuum oven to afford 70 g pure (5RS)-5-(4-methoxyphenyl)-3-methyl-1-oxa-3-azaspiro[5,5]undecane hydrochloride in about 55% yield.

Chemical Structure of the Obtained (5RS)-5-(4-methoxyphenyl)-3-methyl-1-oxa-3-azaspiro[5,5]Undecane Hydrochloride has the Following Analytical Data:

$^1$H NMR (300 MHz, CDCl$_3$): δ/ppm 0.61-1.41 (m, 9H), 2.38 (d, 1H, J=14 Hz), 2.98 (d, 1H, J=10 Hz), 3.10 (d, 1H, J=10 Hz), 3.17 (s, 3H), 3.57 (s, 3H), 3.68 (t, 1H), 4.32 (s, 1H), 4.71 (s, 1H), 6.74 (d, 2H, J=10.0 Hz), 6.95 (d, 2H, J=10.0 Hz).

$^{13}$C NMR (75 MHz, CDCl$_3$): δ/ppm 20.5, 21.2, 24.0, 25.8, 36.0, 37.9, 40.28, 49.0, 51.2, 56.0, 76.8, 77.3, 114.7, 114.7, 129.2, 129.2, 159.6.

IR (λ/cm$^{-1}$): 1036, 1184, 1243, 1460, 1510, 1612, 2941, 3438

Example 3

Preparation of (1RS)-4-[2-(Dimethylamino)-1-(1-hydroxycyclohexyl)ethyl]phenol (Crude O-desmethyl-Venlafaxine)

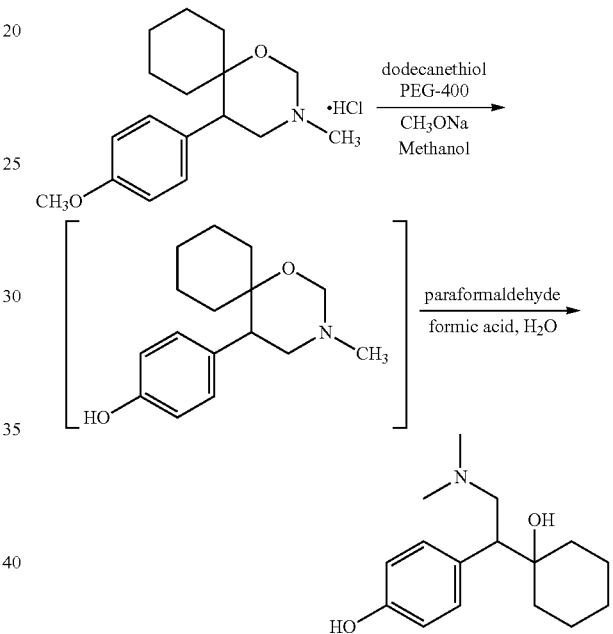

To a solution of 210 ml polyethylene glycol (PEG-400) and 107.52 ml (0.448 moles) of dodecanethiol, a suspension of 82.32 g (1.52 moles) sodium methoxide in 210 ml methanol is added at temperature of about 40-45° C. under stirring. The mixture is stirred for about 30 minutes and a solution of (5RS)-5-(4-methoxyphenyl)-3-methyl-1-oxa-3-azaspiro[5,5]undecane hydrochloride (70 g, 0.224 mol) in 210 ml methanol, is added to the above reaction mixture at temperature of about 145-150° C. under vigorous stirring for about 16-20 hours. The reaction mass is cooled to temperature of about 25-30° C. and 420 ml of D.M. water. Then, 148.96 ml (3.99 moles) of formic acid and 26.9 g (0.9 moles) of paraformaldehyde are added and the mixture is heated at temperature of about 105-115° C. under stirring for about 4 hours. The reaction mass is cooled to temperature of about 25-30° C., extracted with toluene (2×210 ml) and the aqueous layer is treated with 20% w/v aqueous NaOH solution to adjust the pH value at about 8.5-9.5.

In the resulting suspension, 500 ml D.M. water is added, in order to be supplemented, total aqueous volume 910 ml. The suspension is stirred for about 60 minutes at temperature of about 25-30° C. and subsequently for about 60 minutes at temperature of about 5-15° C. The precipitated product is dried in Buchner funnel for about 60 minutes. The cake is washed with 210 ml acetone at temperature of about 50-55° C. under stirring for about 60 minutes, filtered through Buchner funnel, washed with 140 ml acetone and dried in Buchner funnel for about 60 minutes. The treatment with acetone is repeated three times and the collected wet cake is dried in vacuum oven to obtain 45 g (0.17 mol) (1RS)-4-[2-(Dimethylamino)-1-(1-hydroxycyclohexyl)ethyl]phenol hydrochloride in 79% yield.

Chemical Structure of the Obtained (1RS)-4-[2-(Dimethylamino)-1-(1-hydroxycyclohexyl)ethyl]-phenol Hydrochloride has the Following Analytical Data:

$^1$H NMR (500 MHz, DMSO-ds): δ/ppm 0.87-089 (m, 1H), 0.96-1.01 (m, 1H), 1.09-1.15 (m, 1H), 1.27-1.55 (m, 7H), 2.13 (s, 6H), 2.33 (dd, 1H, J=6.3, 12.4 Hz), 2.71 (t, 1H, J=7.9 Hz), 2.98 (dd, 1H, J=8.8, 12.2 Hz), 5.36 (s, 1H), 6.63 (d, 2H, J=8.3 Hz), 6.96 (d, 2H, J=8.3 Hz), 9.11 (s, 1H).

$^{13}$C NMR (125 MHz, DMSO-d$_6$): δ/ppm 21.1, 21.2, 25.6, 32.3, 37.0, 45.2, 45.2, 51.5, 60.3, 72.4, 114.3, 114.3, 130.0, 130.0, 131.6, 155.4.

IR (λ/cm$^{-1}$): 843, 965, 1148, 1272, 1492, 1500, 1518, 1618, 2834, 2865, 2888, 2940, 3424.

| HR-MS (ESI, positive mode): | | |
|---|---|---|
| Chemical structures | Theoretical values | Observed values |
| $[C_{16}H_{26}NO_2]^+$ (M + H$^+$) | 264.19581 | 264.19605 |
| $[C_{16}H_{25}NNaO_2]^+$ (M + Na$^+$) | 286.17775 | 286.17771 |
| $[C_{32}H_{50}N_2NaO_4]^+$ (2M + Na$^+$) | 549.36628 | 549.36623 | wherein

HR-MS=elemental analysis and high resolution mass spectrometry.

Example 4

Preparation of O-desmethyl-Venlafaxine Oxalate

To a mixture of 340 ml acetone and 115 ml water, O-desmethyl-Venlafaxine (45 g, 0.17 mol) is added under stirring. To the resulted suspension, a slurry mixture of oxalic acid (16.2 g, 0.18 mol) with 40 ml acetone and 13.5 ml water is added at temperature of about 25-30° C. The reaction mixture turns into an almost clear solution after about 15 minutes of stirring. The mixture is heated at temperature of about 50-55° C. under stirring for about 30 minutes and then is filtered.

The filtrate is cooled to about 25-30° C. for about 120 minutes, and further cooled to temperature of about 0-4° C. for about 24 hours. The precipitated product is filtered, washed with 27 ml acetone, and dried to obtain 24.8 g (0.07 mol) of O-desmethyl-Venlafaxine oxalate in 41% yield and 99.9% purity by HPLC.

Chemical Structure of the Obtained O-desmethyl-Venlafaxine Oxalate has the Following Analytical Data:

$^1$H NMR (500 MHz, DMSO-d$_6$): δ/ppm 0.93-1.23 (m, 4H), 1.39-1.55 (m, 6H), 2.62 (s, 6H), 2.90 (m, 1H), 3.42 (t, 1H J=11.8 Hz), 3.56 (m, 1H), 6.72 (d, 2H, J=8.4 Hz), 7.12 (d, 2H, J$_1$=8.2 Hz).

$^{13}$C NMR (125 MHz, DMSO-d$_6$): δ/ppm 20.9, 21.2, 25.2, 33.0, 36.0, 43.1, 43.1, 50.1, 58.0, 72.0, 115.0, 115.0, 128.3, 130.3, 130.3, 156.4, 164.3, 164.3.

IR (λ/cm$^{-1}$): 719, 834, 952, 1222, 1271, 1458, 1460, 1475, 1517, 1616, 1720, 2847, 2862, 2938, 3442.

| HR-MS (ESI, positive mode): | | |
|---|---|---|
| Chemical structures | Theoretical values | Observed values |
| $[C_{16}H_{25}N_2O_5]^+$ ([M-(oxalic acid) + H]$^+$) | 264.19581 | 264.19601 |
| $[C_{34}H_{53}N_2O_8]^+$ ([2M-(oxalic acid) + H]$^+$) | 617.37964 | 617.37960 |

Example 5

Recrystallization of O-desmethyl-Venlafaxine Oxalate

A suspension of 20 g of O-desmethyl-Venlafaxine oxalate and 57 ml of acetone is heated to about 60° C. 8.6 ml of ethanol are added drop wisely to the suspension. The cloudy solution is stirred for about 15 minutes at about 60° C. The non-dissolved particles are filtered under reduced pressure. The clear filtrate is gradually cooled to about 0° C. and stirred for about 120 minutes. No crystals are formed. The solution is stirred at temperature of about −20° C. for about 17 hours. The white precipitate is filtered under reduced pressure and washed with 2×85 ml cold acetone. The white solid is dried under vacuum at about 50° C. to obtain 14.5 g O-desmethyl-Venlafaxine oxalate in 73% yield.

Example 6

Preparation of O-desmethyl-Venlafaxine Succinate

Succinic acid (30.45 g, 0.26 mol) is added to a stirred suspension of O-desmethyl-Venlafaxine free base (45 g, 0.17 mol) in a mixed solvent containing 420 ml acetone and 140 ml D.M. water under reflux. The reaction mass became a clear solution and is refluxed further for about 60 minutes. The reaction mixture is cooled gradually at temperature of about 25-30° C. for about 150 minutes and further the mixture is stirred for additional about 150 minutes at temperature of about 10° C. The solid product is filtered under reduced pressure and washed with 70 ml acetone. The product is dried under vacuum at about 50° C. for about 4 hours to obtain 51.3 g (0.13 mol) O-desmethyl-Venlafaxine succinate in 76% yield.

Chemical Structure of the Obtained O-desmethyl-Venlafaxine Succinate has the Following Analytical Data:

$^1$H NMR (500 MHz, DMSO-d$_6$): δ0.84-1.15 (m, 3H), 1.25-1.61 (m, 7H), 2.30 (s, 6H), 2.36 (s, 4H), 2.71 (m, 1H), 2.77 (t, 1H, J=7.3 Hz), 3.18 (dd, 1H, J=6.5, 12.0 Hz), 6.66 (d, 2H, J=8.4 Hz), 7.01 (d, 2H, J=8.3 Hz)

$^{13}$C NMR (125 MHz, DMSO-d$_6$): δ 21.1, 21.2, 25.5, 30.0, 30.0, 32.6, 36.7, 44.5, 44.5, 51.0, 59.5, 72.3, 114.5, 114.5, 130.1, 130.1, 130.4, 155.8, 174.1, 174.1.

IR (Vmax cm$^{-1}$): 835, 953, 1153, 1271, 1390, 1400, 1420, 1450, 1460, 1474, 1636, 2849, 2862, 2932, 2950, 3457

| HR-MS (ESI, positive mode): | | |
|---|---|---|
| Chemical structures | Theoretical values | Observed values |
| $[C_{16}H_{26}NO_2]^+$ ([M-succinic acid + H]$^+$) | 264.19581 | 264.19555 |

Example 7

Recrystallization of O-desmethyl-Venlafaxine Succinate

A mixture of 50 g (0.13 mol) of O-desmethyl-Venlafaxine succinate, 250 ml acetone and 100 ml D.M. water is heated at about 60° C. until clear solution. The hot clear solution is filtered through celite bed, washed with 50 ml hot acetone and is stirred further for about 30 minutes at temperature of about 60° C. The reaction mixture is cooled gradually at temperature of about 25-30° C. for about 120-150 minutes and further is stirred for additional about 120-150 minutes at temperature of about 5-15° C. The precipitated solid is filtered under reduced pressure and washed with 50 ml acetone. The product is dried under vacuum at about 50° C. for about 4 hours to obtain 42.5 g (0.11 mol) O-desmethyl-Venlafaxine succinate in 85% yield.

The present invention describes a large-scale manufacture process for the preparation of O-desmethyl-Venlafaxine and salts or derivatives thereof in high purity at relative low production cost compared to the available processes for producing similar products.

Further, the process of the present invention is safe to operate and benign to the environment. Highly toxic and explosive chemicals, such as n-butyl lithium, lithium aluminum hydride, trialkyl borohydride, which constitute the key ingredients in many of the prior art processes are avoided.

While the present invention has been described with respect to the particular embodiments, it will be apparent to those skilled in the art that various changes and modifications may be made in the invention without departing from the scope thereof, as defined in the appended claims.

The invention claimed is:

1. A process for the preparation of O-desmethyl Venlafaxine, or pharmaceutically acceptable salts, which comprises:
   (a) provision of compound of (5RS)-5-(4-methoxyphenyl)-3-methyl-1-oxa-3-azaspiro[5,5]undecane, namely the spiro-venlafaxine;
   (b) conversion of spiro-venlafaxine into spiro-venlafaxine hydrochloride salt and isolation of said salt in pure form;
   (c) obtaining O-desmethyl Venlafaxine free base in a one-pot process using spiro-venlafaxine hydrochloride salt as starting material, wherein said one-pot process of step is performed by first O-demethylating of the spiro-venlafaxine hydrochloride obtained from step (b) and subsequently treating the reaction mass with paraformaldehyde, formic acid and water at elevated temperature, preferably from about 105° C. to about 1-10° C., to obtain O-desmethyl Venlafaxine free base.

2. The process according to claim 1, wherein it further comprises
   (d) conversion of O-desmethyl Venlafaxine free base into a pharmaceutically acceptable acid additional salt thereof;
   (e) recrystallization of O-desmethyl Venlafaxine salt to obtain crystalline O-desmethyl Venlafaxine salt.

3. The process according to claim 1, wherein the compound of (5RS)-5-(4-methoxyphenyl)-3-methyl-1-oxa-3-azaspiro[5,5]undecane, the spiro-venlafaxine is obtained by hydrogenating 1-[cyano-1-(4-methoxyphenyl)methyl]cyclohexanol followed by ring-closing the hydrogenation product.

4. The process according to claim 3, wherein the ring-closing process is performed by mixing the aqueous solution of the hydrogenation product with paraformaldehyde and formic acid and heating said reaction mixture at moderate temperature, preferably about 55° C.

5. The process according to claim 1, wherein the spiro-venlafaxine hydrochloride salt of step (b) is obtained by treating spiro-venlafaxine with an iso-propanol solution of hydrochloride followed by recrystallization in isopropanol.

6. The process according to claim 1, wherein the O-desmethylating process of step (c) is carried out using alkane thiolate anion in the presence of high molecular weight polyol and alcoholic solvent.

7. The process according to claim 2, wherein said O-desmethyl Venlafaxine free base is reacted with oxalic acid to form the oxalate salt of O-desmethyl Venlafaxine and said O-desmethyl Venlafaxine oxalate solid is re-crystallized using acetone/ethanol.

* * * * *